US011638611B2

(12) United States Patent
Babazade et al.

(10) Patent No.: US 11,638,611 B2
(45) Date of Patent: May 2, 2023

(54) SYSTEMS AND METHODS FOR LOCATING AN INSERTED CATHETER TIP

(71) Applicants: Rovnat Babazade, League City, TX (US); Yuriy Petrov, Galveston, TX (US); Irene Petrov, Galveston, TX (US); Rinat O. Esenaliev, League City, TX (US)

(72) Inventors: Rovnat Babazade, League City, TX (US); Yuriy Petrov, Galveston, TX (US); Irene Petrov, Galveston, TX (US); Rinat O. Esenaliev, League City, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 613 days.

(21) Appl. No.: 16/402,493

(22) Filed: May 3, 2019

(65) Prior Publication Data
US 2020/0345985 A1 Nov. 5, 2020

(51) Int. Cl.
*A61B 34/20* (2016.01)
*A61B 5/00* (2006.01)
(Continued)

(52) U.S. Cl.
CPC .............. *A61B 34/20* (2016.02); *A61B 90/37* (2016.02); *A61M 25/0105* (2013.01);
(Continued)

(58) Field of Classification Search
None
See application file for complete search history.

(56) References Cited

U.S. PATENT DOCUMENTS 6,190,370 B1 2/2001 Tsui
7,068,867 B2 6/2006 Adoram
(Continued)

FOREIGN PATENT DOCUMENTS

EP 2701624 3/2014
WO WO 2019/136412 * 7/2019 ............... A61B 8/00

OTHER PUBLICATIONS

Xia et al., "Fiber optic photoacoustic probe with ultrasonic tracking for guiding minimally invasive procedures", Opto-Acoustic Methods and Applications in Biophotonics II, Proc. of SPIE vol. 9539, 2015, pp. 1-5 (Year: 2015).*
(Continued)

*Primary Examiner* — James M Kish
(74) *Attorney, Agent, or Firm* — Thomas Horstemeyer, LLP

(57) ABSTRACT

In one embodiment, a system for locating a tip of a catheter that has been inserted into a patient includes an implantable catheter having a distal tip, a pulsed light source that is co-located with the distal tip of the implantable catheter, the pulsed light source being configured to emit pulses of light into surrounding patient tissue, an optoacoustic sensor configured to be applied so a skin surface of the patient at a position proximate to the pulsed light source and to sense optoacoustic waves generated when the pulses of light are absorbed by the surrounding patient tissue, and an optoacoustic console configured to receive optoacoustic wave signals from the optoacoustic sensor and to display an indication of the optoacoustic wave signals to a medical professional to provide an indication of the location of the pulsed light source and, therefore, the distal tip of the implantable catheter.

18 Claims, 3 Drawing Sheets

(51) Int. Cl.
*A61M 25/01* (2006.01)
*A61B 90/00* (2016.01)
*A61B 90/30* (2016.01)
*A61M 25/00* (2006.01)
*A61B 17/34* (2006.01)
*G10K 15/04* (2006.01)

(52) U.S. Cl.
CPC ......... *A61B 5/0095* (2013.01); *A61B 17/3401* (2013.01); *A61B 2034/2063* (2016.02); *A61B 2090/062* (2016.02); *A61B 2090/306* (2016.02); *A61M 2025/0007* (2013.01); *A61M 2025/0166* (2013.01); *A61M 2205/0294* (2013.01); *A61M 2210/1003* (2013.01); *G10K 15/046* (2013.01)

(56) References Cited

U.S. PATENT DOCUMENTS

| | | | | |
|---|---|---|---|---|
| 2003/0130577 | A1* | 7/2003 | Purdy | A61B 17/1214 600/433 |
| 2004/0131299 | A1* | 7/2004 | Adoram | A61B 8/0841 385/12 |
| 2006/0206178 | A1 | 9/2006 | Kim | |
| 2011/0017217 | A1 | 1/2011 | Wood | |
| 2012/0203101 | A1 | 8/2012 | Prough | |
| 2014/0058253 | A1 | 2/2014 | Prough | |
| 2014/0275990 | A1* | 9/2014 | Hagy | A61B 90/98 600/424 |
| 2014/0378796 | A1* | 12/2014 | Chen | A61B 5/7278 600/328 |
| 2015/0201944 | A1* | 7/2015 | Starnes | A61B 17/1204 606/194 |
| 2016/0287133 | A1* | 10/2016 | Eichler | A61B 5/0044 |

OTHER PUBLICATIONS

Kang et al., "Needle visualization using photoacoustic effect", SPIE BiOS, Proc. of SPIE vol. 9323, 2015, pp. 1-7 (Year: 2015).*
Hermanides, et al., "Failed epidural: causes and management", British Journal of Anaesthesia 109 (2): 144-54 (2012).
Elsharkwawy, et al., "Preliminary experience with epidural and perineural catheter localization with pulsed wave Doppler ultrasonography", Minerva anestesiologica, 84(7), 2018.

* cited by examiner

SYSTEMS AND METHODS FOR LOCATING AN INSERTED CATHETER TIP

CROSS-REFERENCE TO RELATED APPLICATION

This application is a continuation of copending U.S. Non-Provisional Application having Ser. No. 16/393,529, entitled, "Systems And Methods For Locating An Inserted Catheter Tip," and filed Apr. 24, 2019 and is herein incorporated by reference in its entirety.

BACKGROUND

Over 234 million major surgical procedures are performed every year worldwide. In many of these procedures, catheters are inserted into the body to deliver anesthesia to the patient. For example, approximately 2.4 million women receive neuraxial blocks (i.e., epidural or spinal anesthesia) with epidural catheters annually in the United States. Unfortunately, failure of epidural anesthesia and analgesia occurs in nearly 30% of cases in clinical practice. Improper placement of the tip of the catheter is the primary reason for such failures. When failure occurs, the catheter must be removed and a new catheter must be inserted.

Verification of proper placement of the catheter at the time of insertion and afterward is challenging. Various techniques have been developed to locate the tip of peripheral nerve and epidural catheters placed within the body, including ultrasound, x-rays, and fluoroscopy. However, each of these techniques has its limitations. First, not every technique is appropriate for every patient. For example, while epidural catheters are commonly used for labor analgesia, pregnant women cannot be exposed to the x-rays or fluoroscopy. Second, even when a technique is appropriate for use on a given patient, the technique may still not be effective. For example, it is extremely difficult to locate a catheter tip positioned behind bony structures using ultrasound. In short then, there is no current "gold standard" technique for locating a peripheral nerve or epidural catheter tip in real time during a medical procedure.

In view of the above facts, it can be appreciated that it would be desirable to have an effective system and method for locating a catheter tip that is inserted within a patient's body.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have an effective system and method for locating a catheter tip that is inserted within a patient's body. Disclosed herein are examples of such a systems and methods. In some embodiments, a system comprises a catheter, such as an epidural catheter, which is configured for insertion into a patient's body, such as within the epidural space. Associated with a distal tip of the catheter is a light source that emits pulsed light into the surrounding tissues. In some embodiments, the light source can comprise the distal tip of an optical waveguide that is co-located with the catheter tip. Also included in the system is an acoustic sensor that can be applied to the patient's skin over an anticipated location of the catheter tip. The sensor is configured to sense optoacoustic waves that propagate through the patient's tissues responsive to the emitted light pulses. These acoustic waves can be used to identify the location of the catheter tip within the patient. In some embodiments, optoacoustic wave signals can be displayed to the medical professional (e.g., anesthesiologist or surgeon) using an optoacoustic console to which the sensor is connected. The location of the catheter tip can then be determined by identifying the point on the body at which the optoacoustic wave signals are strongest, which indicates the point at which the distance between the sensor and the catheter tip is smallest.

In the following disclosure, various specific embodiments are described. It is to be understood that those embodiments are example implementations of the disclosed inventions and that alternative embodiments are possible. Such alternative embodiments include hybrid embodiments that include features from different disclosed embodiments. All such embodiments are intended to fall within the scope of this disclosure.

Figure 1:
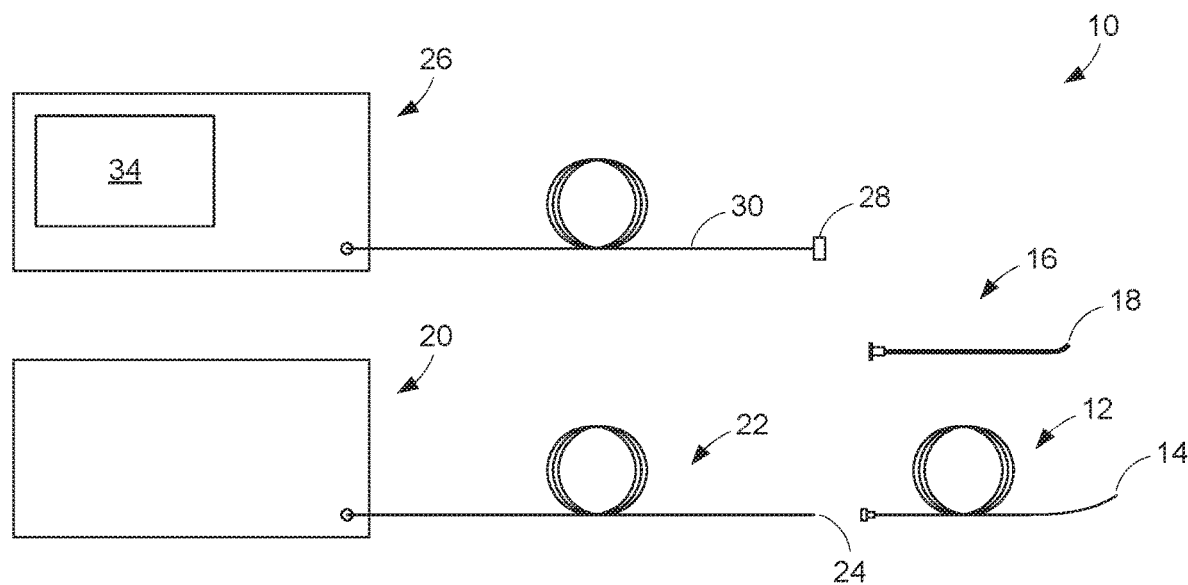
FIG. 1 is a schematic diagram of an embodiment of a system for locating a catheter tip within a patient's body.

FIG. 1 illustrates an embodiment of a system 10 for locating a catheter tip within a patient's body. In some embodiments, the various components of the system 10 (or at least some of them) can be grouped together and provided as a "kit" (or part of a kit) with which a surgical procedure that requires delivery of anesthesia to a patient using an inserted (implanted) catheter. As shown in FIG. 1, the system 10 includes an implantable catheter 12 having a distal tip 14 that can be placed within the body, a needle 16 having a distal tip 18 that can also be placed within the body, a pulsed light generator 20 from which extends an optical waveguide 22 also having a distal tip 24 that can be placed within the body, and an optoacoustic console 26 that is connected to an optoacoustic sensor 28 that is provided on a distal end of an electrical cable 30 that extends from the console.

The nature of the catheter 12 depends upon the particular application in which it is used. In cases in which the catheter 12 is an epidural catheter that is to be used to provide epidural anesthesia, the catheter can comprise a flexible, small diameter rubber or polymeric catheter. By way of example, the catheter 12 can have a French gauge of approximately 18 to 21 Fr and has a length that is long enough to reach a desired location within the body with ample length extending from the body.

The optical waveguide 22 can, for example, comprise an optical fiber having an inner core that is surrounded by an outer cladding. In general, the optical waveguide 22 is smaller than the catheter 12. By way of example, the optical waveguide 22 can have an outer diameter of approximately 100 to 400 μm.

Figure 2A:
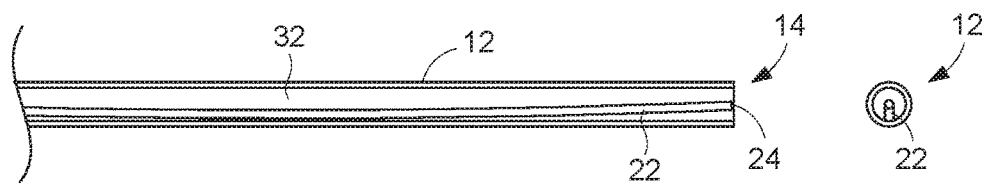
FIG. 2A is a first example embodiment of an implantable catheter that can be used in the system of FIG. 1, illustrating co-location of a pulsed light source with a distal tip of the catheter.
Figure 2B:
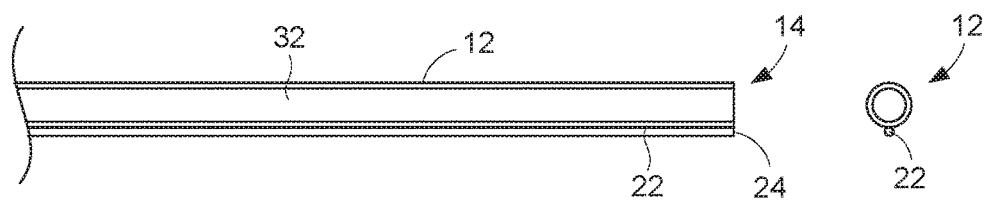
FIG. 2B is a second example embodiment of an implantable catheter that can be used in the system of FIG. 1, illustrating co-location of a pulsed light source with a distal tip of the catheter.
Figure 2C:
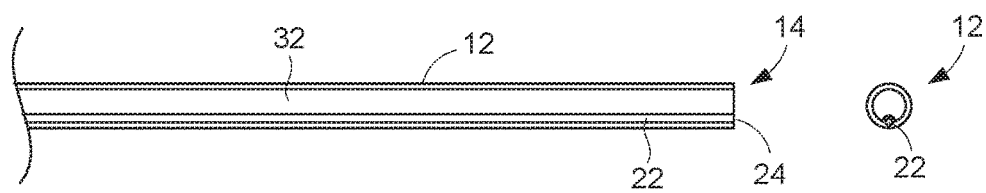
FIG. 2C is a third example embodiment of an implantable catheter that can be used in the system of FIG. 1, illustrating co-location of a pulsed light source with a distal tip of the catheter.

As identified above, the tip 24 of the optical waveguide 22 can be co-located with the tip 14 of the catheter 12 for purposes of identifying a location of the catheter tip within the body. As described below, pulsed light generated by the pulsed light generator 20 and emitted from the optical waveguide tip 24 can be used to create optoacoustic waves that travel through the patient's tissues, and the strength of those waves can be used to determine the location of the co-located catheter tip 14. Co-location of the optical waveguide tip 24 and the catheter tip 14 can be achieved in a variety of ways. FIGS. 2A-2C illustrate three examples, which are described below.

In a first example illustrated in FIG. 2A, the optical waveguide 22 can be extended through an inner lumen 32 of the catheter 12 so that the tip 24 of the optical waveguide 22 is positioned in close proximity to the tip 14 of the catheter 12. In such a case, the catheter 12 may be placed within the body independent of the optical waveguide 22, if desired. For example, after the catheter 12 has been inserted into the body, the optical waveguide 22 can be fed through the catheter until the two tips 24 and 14 are co-located. In such a case, one would keep track of the length of the catheter 12 that is within the body as well as the length of optical waveguide 22 that is fed through the catheter to ensure such co-location.

With reference to FIG. 2B, the optical waveguide 22 is provided on an outer surface of the catheter 12. In such a case, the optical waveguide 22 can either be integrated with the catheter 12 during fabrication of the catheter, or can be secured to the catheter after it has been fabricated. In either case, the tip 24 of the optical waveguide 22 is fixed so as to be co-located with the tip 14 of the catheter 12.

Referring next to FIG. 2C, the optical waveguide 22 is located within the catheter 12. In some embodiments, the optical waveguide 22 is integrated with the wall of the catheter 12 during fabrication of the catheter. In other embodiments, the optical waveguide 22 is extended through an auxiliary lumen formed within the wall of the catheter 12. In still other embodiments, the optical waveguide is secured to the wall of the catheter 12 within the inner lumen 32. Regardless of the particular configuration used, the tip 24 of the optical waveguide 22 is fixed so as to be co-located with the tip 14 of the catheter 12.

It is noted that, in each of the above examples, the catheter 12 can comprise indicia in the form of depth markings that assist the medical professional in determining the length of catheter that has been inserted into the body. It is further noted that, while the use of an optical waveguide 22 has been described, in alternative embodiments a light emitting element can be provided at the tip 14 of the catheter 12. For example, a light-emitting diode can be mounted to or integrated with the catheter tip 14 and wires necessary for its operation can extend through either the inner lumen 32 or the wall of the catheter. In such an embodiment, the optical waveguide 22, as well as the pulsed light generator 20, would not be necessary.

The needle 16 can be used to introduce the implantable catheter 12 into the body. In cases in which the catheter 12 is an epidural catheter that is to be placed within the epidural space, the needle 16 can comprise a Tuohy needle. Such a needle typically has a gauge of approximately 16 to 25 Ga (e.g., 19 Ga). As shown in FIG. 1, the tip 18 of the needle 16 can have a slight upward curvature to it that facilitates insertion of the catheter 12 in an upward direction within the epidural space (i.e., toward the patient's head). It is noted that, like the catheter 12, the needle 16 can comprise indicia in the form of depth markings that assist the medical professional in determining the length of catheter that has been inserted into the body.

The pulsed light generator 20 can comprise a laser generator that generates pulsed laser light. The pulsed laser light can be within the infrared spectrum, i.e., light having a wavelength of approximately 750 nm to 1 mm. In some embodiments, the pulsed light is within the near- to mid-infrared spectrum from 750 nm to 2,500 nm. By way of example, the pulsed light generator can comprise a q-switched solid-state laser having a central wavelength of 1,535 nm.

The optoacoustic sensor 28 can comprise any component that is capable of sensing the optoacoustic waves generated within the patient's tissue. In some embodiments, the optoacoustic sensor 28 comprises a piezoelectric element.

The optoacoustic console 26 is configured to receive optoacoustic wave signals from the optoacoustic sensor 28 when the sensor is placed upon the patient's body in proximity to the implanted catheter tip 14 as light is emitted from the optical waveguide tip 24 (or other pulsed light source). In some embodiments, the optoacoustic waves are ultrasonic waves. As indicated in FIG. 1, the optoacoustic console 26 can include a display 34 with which information, such as a graphical depiction of the received optoacoustic wave signals, can be presented to the medical professional in real time for consideration.

An exemplary system 10 having been described above, an example of use of the system in locating the tip 14 of the catheter 12 will now be discussed. For this discussion, epidural anesthesia will be used as an example application. It is noted, however, that neither the disclosed systems nor the disclosed methods are limited to that particular application.

When anesthesia is to be administered to the epidural space, the patient's back is shaved and cleaned in preparation for the insertion procedure. The patient can either be in a seated position or lying on his or her side with the back exposed and easily accessible. Next, a local anesthetic, such as lidocaine, can be injected at the site at which the needle 16 is to be inserted.

Figure 3:
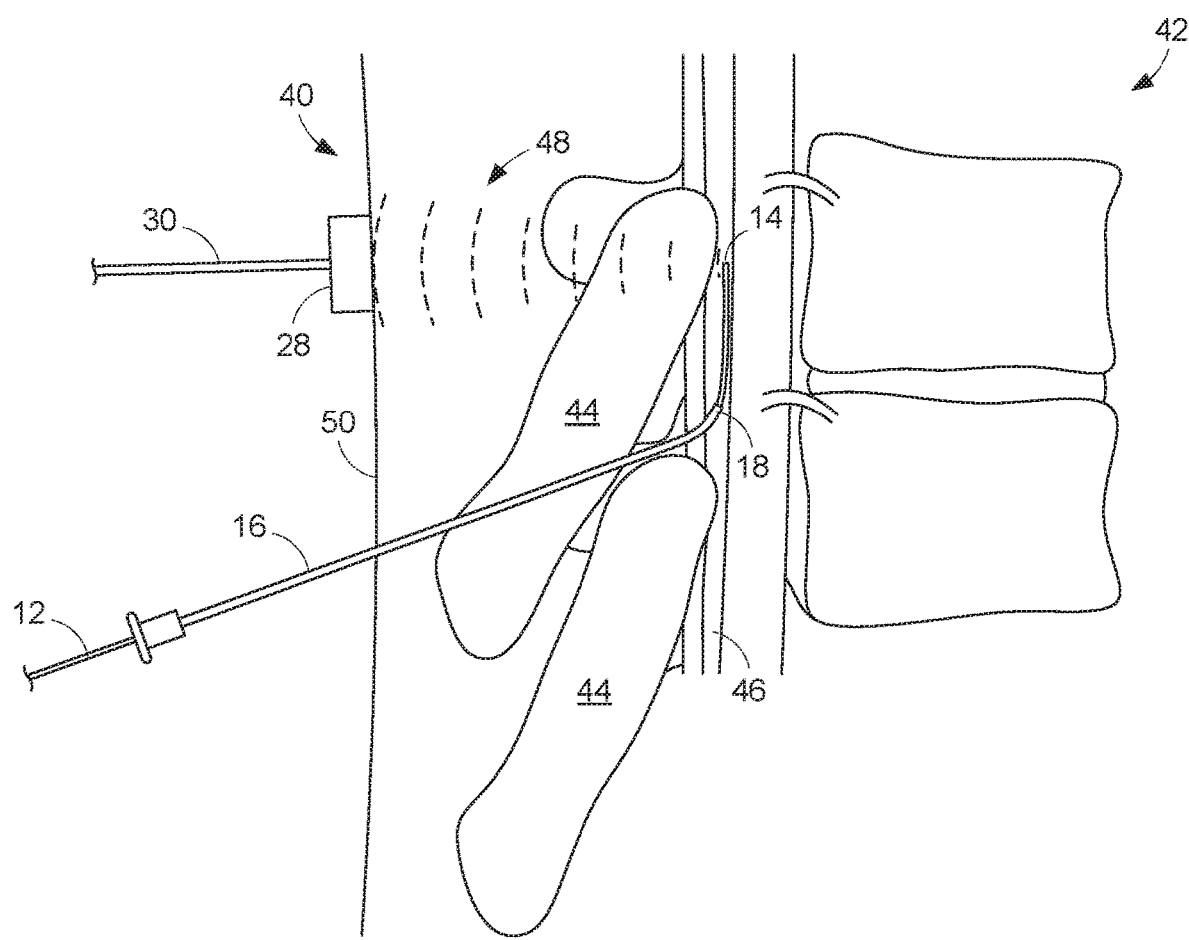
FIG. 3 is a schematic diagram illustrating an embodiment of locating a distal tip of a catheter that has been inserted into a patient's body.

As illustrated in FIG. 3, the needle 16 can be inserted through the patient's back 40 and toward the spine 42, passing the needle between lumbar vertebrae 44. The needle 16 is slowly advanced through the patient's tissues until, after approximately 5 to 6 cm of insertion, the epidural space 46 is reached. Once the needle 16 is in that position, the catheter 12 can be advanced through the needle so that the tip 14 of the catheter also enters the epidural space 46. The catheter 12 can then be advanced to the point at which its tip 14 is positioned approximately 3 to 5 cm beyond the tip 18 of the needle 16. As indicated in FIG. 3, the upward curvature of the needle tip 18 helps ensure that the catheter 12 traverses the epidural space 46 along its central longitudinal axis and toward the patient's head (upward in the orientation of FIG. 3).

At this point, the catheter tip 14 should be located within the epidural space 46 at the midline of the patient's back (i.e., within the patient's sagittal plane). This location can be confirmed using the pulsed light source co-located at the catheter tip 14. In particular, pulsed light, such as pulsed laser light, can be emitted from the catheter tip 14 and into the tissues that surround it. When the pulsed light encounters a chromophore or pigment (e.g., water), the light is absorbed and produces an optoacoustic wave (i.e., a pressure wave) that is detectable as an acoustic response. The frequency of the waves depends upon the wavelength and duration of the pulsed light. In some embodiments, the pulsed light can be tuned to induce ultrasonic waves that travel in straight lines from the source with minimal scattering and attenuation, thereby providing both lateral resolution and axial resolution regarding the size and shape of the source.

The optoacoustic waves generated by the pulsed light source are depicted in FIG. 3 with dashed lines 48. As is further depicted in that figure, the waves 48 travel through the patient's tissues to the patient's skin surface 50. When the optoacoustic sensor 28 is applied to the skin surface 50, it senses these waves 48 and an optoacoustic wave signal is transmitted to the optoacoustic console 26. The console 26 can then display a graphical representation of the optoacoustic wave signal in its display 34, which is visible to the medical professional. The position of the sensor 28 on the skin surface 50 initially can be selected based upon the anticipated position of the catheter tip 14 beneath the surface. In some embodiments, the medical professional can move the sensor 28 along the skin surface 50 while simultaneously monitoring the display 34 to identify the point at which the signal is strongest. It is at that point that the catheter tip 14 is located. In other embodiments, multiple sensors 28 can be placed on the patient's back 40 at discrete positions around the expected location of the catheter tip 14 and an algorithm executed by the optoacoustic console 26 can automatically calculate the location of the catheter tip based upon the various signals received from the sensors. It is further noted that, in some embodiments, the optoacoustic console 26 can also automatically calculate the depth of the catheter tip 14 within the body based upon the speed of propagation of the waves through the tissues and the delay between light pulses and sensed waves.

Once the location of the catheter tip 14 can been determined, the medical professional can decide whether or not the location is acceptable. Again, the goal is typically a location that is along the midline of the back upward (toward the head) along the spine. Assuming that the catheter tip 14 is in such a position, the needle 16 can be withdrawn leaving the catheter 12 in place and anesthesia can be delivered to the epidural space 46 using the catheter.

Experiments were performed using a system similar to that described above. In these experiments, a freshly euthanized pig having a mass of 30 kg was used as a "patient" upon which to test the system. An optical fiber was fed through an epidural catheter so as to co-locate the fiber tip with the catheter tip. A pulsed solid-state laser system was used to generate pulsed light having a wavelength of 1535 nm, a pulse duration of 10 ns, a repetition rate of 1 Hz, and an average pulse energy of 0.5 mJ. A custom-made optoacoustic sensor, in the form of a piezoelectric transducer, was used to locate the tip of the fiber and, therefore, the tip of the catheter within the pig's body.

A needle was inserted into the pig's epidural space until resistance was lost and then the catheter was passed through the needle so as to position its tip within the epidural space. The laser system was activated so as to generate the pulsed light and then the optoacoustic sensor was moved along the spine. Custom-made software was used to calculate the distance of the sensor from the catheter tip. The signal obtained from the optoacoustic console increased as the sensor approached the location of the fiber tip. The sensor was moved to the position at which the calculated distance between the sensor and the catheter tip was smallest and a measurement was taken on the surface of the spine of the distance between the needle/catheter insertion point and the sensor location ($\Delta y$). After that, the sensor was moved tangential to the spine. When the shortest distance to the catheter tip was found in this case, a measurement was taken between the central spine line and the sensor position ($\Delta x$).

Figure 4:
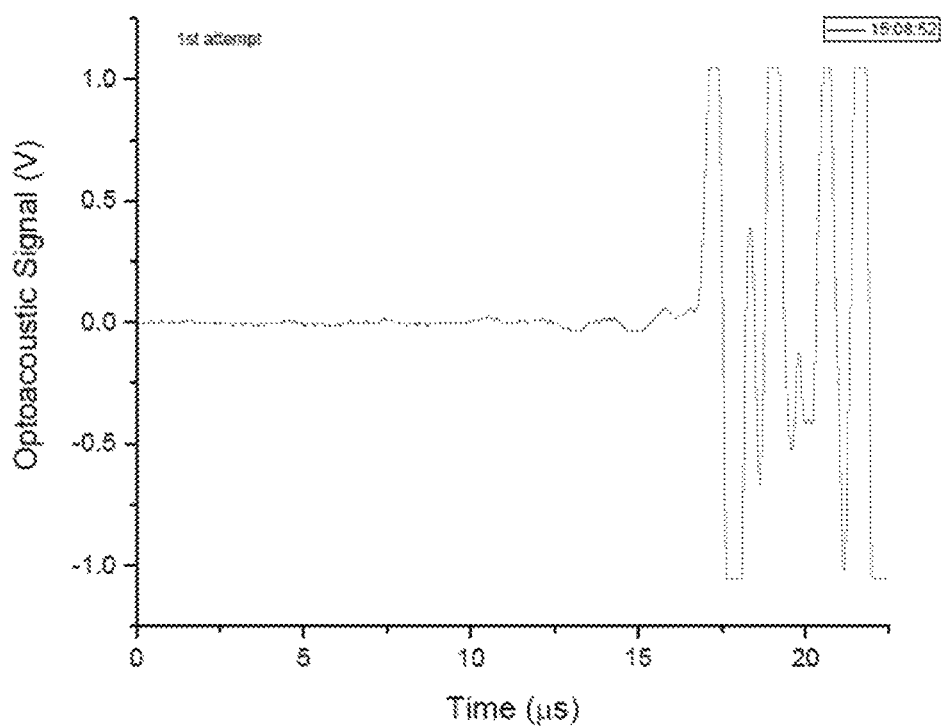
FIG. 4 is a graph that plots optoacoustic waves detected using a system similar to that of FIG. 1 in a first experiment.

In a first case, the needle was inserted 3.5 cm into the spine. The epidural catheter was then advanced through the needle but encountered resistance, indicating that it may have curled up after exiting the needle. The tip of the catheter was determined to be close to the insertion point, i.e., $\Delta x=1$ cm, $\Delta y=0$ cm. The detected waves at the location of the catheter tip were determined to have a travel time of 17.2 ps. Assuming the speed of sound in soft tissue to be 1.5 mm/µs, this indicates that the catheter tip was at a depth of 2.6 cm. The amplitude of the signal was very high (out of scale). This is apparent from FIG. 4, which shows the pattern recorded from the optoacoustic console.

Figure 5:
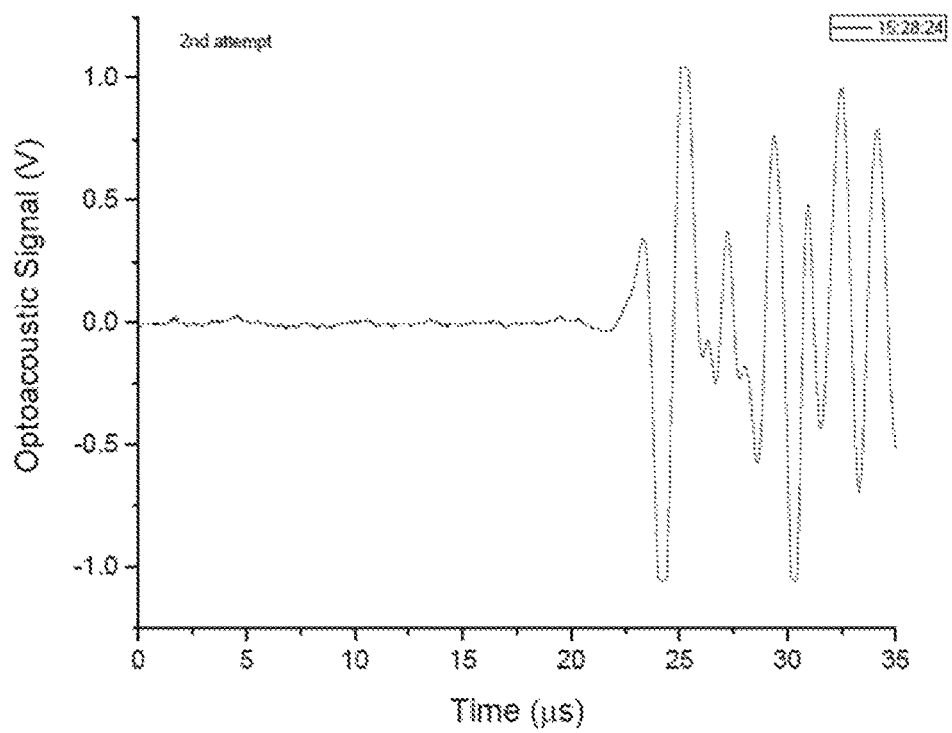
FIG. 5 is a graph that plots optoacoustic waves detected using a system similar to that of FIG. 1 in a second experiment.

In a second case, the needle was inserted in the lower part of the pig's spine at a depth of 4 cm. The epidural catheter was advanced 12 cm though the needle (i.e., 4 cm in the needle and 8 cm into the epidural space). The position of the catheter tip was determined to be a $\Delta x=1.5$ cm and $\Delta y=8$ cm. The catheter tip was then determined to be at a depth of 3.6 cm. The amplitude of the signal at that point was very high (out of scale), as shown in FIG. 5.

These data indicate that the disclosed optoacoustic system is capable of detecting even slight displacement of the pulsed light source, and therefore the catheter tip, relative to overlying tissues. It is anticipated that an optoacoustic method using such a system can provide sub-millimeter accuracy of catheter placement as well as position monitoring during a medical procedure.

The invention claimed is:

1. A system for locating a position of a tip of an inserted catheter along a patient's body by determining a position on the patient's skin surface that is closest to the catheter tip, the system comprising:
   an epidural catheter having a distal tip;
   a pulsed light source that is co-located with the distal tip of the epidural catheter, the pulsed light source being configured to emit pulses of light into surrounding patient tissue;
   an optoacoustic sensor configured to be applied to various positions on a skin surface of the patient at an anticipated location of the catheter distal tip along the patient's body and to sense optoacoustic waves generated when the pulses of light emitted by the pulsed light source are absorbed by patient tissue surrounding the catheter distal tip; and
   an optoacoustic console configured to receive optoacoustic wave signals from the optoacoustic sensor and to display graphical depictions of the received optoacoustic wave signals to a medical professional, wherein the position of the optoacoustic sensor on the patient's skin surface that generates the strongest displayed optoacoustic wave signal identifies to the medical professional the position along the patient's body at which the catheter distal tip is located.

2. The system of claim 1, wherein the epidural catheter has a French gauge of approximately 18 to 21 Fr.

3. The system of claim 1, wherein the pulsed light source comprises a tip of an optical waveguide that is co-located with the distal tip of the epidural catheter.

4. The system of claim 3, further comprising a pulsed light generator that generates pulsed light that is transmitted through the optical waveguide.

5. The system of claim 4, wherein the pulsed light generator is a laser generator configured to generate laser light pulses is within the infrared spectrum.

6. The system of claim 3, wherein the optical waveguide is an optical fiber.

7. The system of claim 6, wherein the optical fiber is positioned within an inner lumen of the epidural catheter.

8. The system of claim 6, wherein the optical fiber is attached to the epidural catheter.

9. The system of claim 6, wherein the optical fiber is integrated into the epidural catheter.

10. The system of claim 1, wherein the optoacoustic sensor comprises a piezoelectric element.

11. A method for locating a position of a tip of an inserted catheter along a patient's body by determining a position on the patient's skin surface that is closest to the catheter tip, the method comprising:
    inserting a needle into an epidural space of the patient's body, the needle having a distal tip and an open inner lumen;
    inserting an epidural catheter through the inserted needle and into the patient's epidural space beyond the distal tip of the needle, the catheter having a pulsed light source co-located with a distal tip of the catheter;
    emitting pulsed light from the pulsed light source;
    placing an optoacoustic sensor on the skin of the patient at an anticipated location along the patient's body of the tip of the epidural catheter and moving the sensor to different positions at the anticipated location;
    receiving optoacoustic wave signals produced within the tissues of the patient in response to the emitted pulsed light being absorbed by the tissues at each position on the patient's skin; and
    displaying graphical depictions of the optoacoustic wave signals to a medical professional, wherein the position of the optoacoustic sensor on the patient's skin that generates the strongest displayed optoacoustic wave signal identifies to the medical professional the position along the patient's epidural space at which the epidural catheter distal tip is located.

12. The method of claim 11, wherein the needle is a Tuohy needle.

13. The method of claim 12, wherein placing an optoacoustic sensor on the skin comprises placing the optoacoustic sensor on the skin of the patient's lower back.

14. The method of claim 11, wherein the pulsed light source comprises a tip of an optical fiber that is co-located with the tip of the epidural catheter.

15. The method of claim 14, wherein the optical fiber extends through an inner lumen of the epidural catheter.

16. The method of claim 14, wherein the optical fiber is integrated with the epidural catheter.

17. The method of claim 11, wherein emitting pulsed light comprises emitting pulsed laser light within the infrared spectrum.

18. A system for locating a position of a tip of an inserted catheter along a patient's epidural space by determining a position on the patient's skin surface that is closest to the catheter tip, the system comprising:
    a needle having a distal tip and an open inner lumen, the needle being configured to be passed through the patient until the distal tip of the needle is positioned within the patient's epidural space;
    an implantable catheter having a distal tip, the implantable catheter being configured to be passed through the open inner lumen of the needle and extended beyond the distal tip of the needle and into the patient's epidural space;
    a pulsed light source that is co-located with the distal tip of the implantable catheter, the pulsed light source being configured to emit pulses of light into surrounding patient tissue;
    an optoacoustic sensor configured to be applied to various positions on a skin surface of the patient at an anticipated location of the catheter distal tip along the patient's body and to sense optoacoustic waves generated when the pulses of light emitted by the pulsed light source are absorbed by patient tissue surrounding the catheter distal tip; and
    an optoacoustic console configured to receive optoacoustic wave signals from the optoacoustic sensor and to display graphical depictions of the received optoacoustic wave signals to a medical professional, wherein the position of the optoacoustic sensor on the patient's skin surface that generates the strongest displayed optoacoustic wave signal identifies to the medical professional the position along the patient's epidural space at which the catheter distal tip is located.

* * * * *